United States Patent [19]
Sakurai et al.

[11] Patent Number: 6,124,258
[45] Date of Patent: Sep. 26, 2000

[54] IRON-CASEIN COMPLEX AND PROCESS FOR PREPARING THE SAME

[75] Inventors: Toshio Sakurai, Tokyo; Toshiaki Uchida, Saitama; Kazumasa Hamashita, Saitama; Akira Tomizawa, Saitama, all of Japan

[73] Assignee: Snow Brand Milk Products Co., Ltd., Japan

[21] Appl. No.: 09/194,305

[22] PCT Filed: Mar. 24, 1997

[86] PCT No.: PCT/JP97/00963

§ 371 Date: Jul. 14, 1999

§ 102(e) Date: Jul. 14, 1999

[87] PCT Pub. No.: WO98/42745

PCT Pub. Date: Oct. 1, 1998

[51] Int. Cl.$^7$ ............ A61K 38/16; C07F 15/00
[52] U.S. Cl. ............ 514/6; 530/400; 530/832; 556/148
[58] Field of Search ............ 530/400, 832; 556/148; 514/6

[56] References Cited

U.S. PATENT DOCUMENTS 5,606,086  2/1997  Dosako et al. ............ 556/138

FOREIGN PATENT DOCUMENTS

| 0 656 366 A1 | 6/1995 | European Pat. Off. . |
| 02083400 A2 | 3/1990 | Japan . |
| WO 94/19375 | 9/1994 | WIPO . |

*Primary Examiner*—Porfirio Nazario-Gonzalez
*Attorney, Agent, or Firm*—Testa, Hurwitz & Thibeault, LLP

[57] ABSTRACT

Iron-casein complexes and methods for preparation thereof without iron characteristic astringent taste even by heat sterilization and having high iron supplying effect.

The iron-casein complexes can be obtained by mixing three components of solution A containing i) carbonic acid, ii) hydrogencarbonic acid or iii) their mixtures, solution B1 containing iron, and solution B2 containing caseins in a suitable order.

The resultant iron-casein complexes contain 1–1,000 atoms of iron and one molecule or over of carbonic acid and/or hydrogencarbonic acid for one molecule of caseins without exhibiting astringent taste even by heat sterilization. The iron-casein complexes exhibit superior anemia preventive effect than those of inorganic iron salts.

19 Claims, No Drawings

IRON-CASEIN COMPLEX AND PROCESS FOR PREPARING THE SAME

This application is the National Stage of International Application No. PCT/JP97/00963, filed Mar. 24, 1997.

FIELD OF THE INVENTION

This invention relates to carbonic acid- and/or hydrogencarbonic acid-iron-casein complexes and methods for preparation thereof. The carbonic acid- and/or hydrogencarbonic acid-iron-casein complexes of the present invention have a characteristic feature that these complexes do not exhibit iron specific astringent taste even sterilization by heating and are useful for prevention and treatment of anemia, and materials for preparation of iron enriched foods, medicines and feeds.

BACKGROUND OF THE INVENTION

The iron uptake of Japanese has been maintaining about 100% sufficiency rate for requirement ever since 1975 and iron is deemed as one of the essential nutritional elements that must be carefully taken up with meals. In world-wide point of view, individuals in advanced industrial countries suffer a deficiency of iron, thus supply of iron enriched foods or medicines for persons with anemic tendency and pregnant and breast feeding females is desired. However, iron salts generally used for enrichment such as iron sulfate or iron citrate produce of iron characteristic astringent taste and adverse reactions such as disturbance of gastrointestinal mucosa, thus, the amount to be added is limited. Organic iron compounds such as heme-iron also have problems of taste such as metallic and fishy taste, and their addition to foods face many restricted conditions.

Addition of milk casein, amino acids or casein phosphopeptide or the like has been tried for stimulation of iron absorption (Japanese Laid-open Patent Application No. 162843 (1984)). However, these methods could not diminish the astringent taste of iron compounds, furthermore, reduced amount of addition of iron failed to diminish the astringent taste of iron.

The inventors of the present invention already succeeded to reduce characteristic astringent taste of iron by combining iron and casein (Japanese Laid-open Patent Application No. 83400 (1990)). However, the prepared iron casein complex has poor heat stability exhibited iron characteristic astringent taste following heat sterilization at 90° C. for 10 minutes or 120° C. for 2–3 seconds, or retort sterilization. Therefore, application of the iron casein complex to foods demand sterilization of production line and causes poor cost effectiveness. The characteristic astringent taste of the iron casein complex caused by heat sterilization may be due to the release of iron from weak iron and casein binding, and formation of iron hydroxides. Thus, a more firm heat resistant binding of iron and casein without exhibiting iron characteristic astringent taste even following heat sterilization was developed.

This invention aims to provide pharmaceutical iron preparations as food additives free from iron characteristic astringent taste even following heat sterilization. That is, one object of the present invention is to provide carbonic acid- and/or hydrogencarbonic acid-iron-casein complexes and methods for preparation thereof.

DISCLOSURE OF THE INVENTION

The inventors of the present invention found that carbonic acid- and/or hydrogencarbonic acid-iron-casein complexes can be formed by mixing a solution containing carbonic or hydrogencarbonic acid ion and a solution containing caseins and iron ion, and the resultant carbonic acid- and/or hydrogencarbonic acid-iron-casein complexes contain iron at high ratios without exhibiting iron characteristic astringent taste.

The present invention relates to carbonic acid- and/or hydrogencarbonic acid-iron-casein complexes containing 1–1,000 atoms of iron and one or more molecules of carbonic acid and/or hydrogencarbonic acid to one molecule of caseins. These complexes have a characteristic feature without exhibiting iron characteristic astringent taste even following heat sterilization.

These complexes can be obtained by mixing a solution containing i) carbonic acid, or ii) hydrogencarbonic acid, or iii) carbonic acid and hydrogencarbonic acid (Solution A), and a solution containing iv) iron (Solution B1) and, a solution containing v) caseins (Solution B2). The molar concentration of iron ion in vi) solution B1 is $\frac{1}{3}$ or less, preferably $\frac{1}{10}$, more preferably $\frac{1}{30}$, far more preferably $\frac{1}{60}$ and most preferably $\frac{1}{100}$ to those of carbonic acid and hydrogencarbonic acid dissolved in a mixed solution of A, B1 and B2. The molar number of caseins in vii) solution B2 must be 1–1/1000 to that of iron ion in solution B1.

In addition, solutions A, B1 and B2 may be simultaneously mixed, or by mixing solutions A and B2 and then by addition of solution B1 to the mixed solution. Alternatively, solutions B1 and B2 are mixed and then solution A is added to the mixed solution or vice versa. Furthermore, some amounts of carbonic acid and/or hydrogencarbonic acid beyond their solubility may be contained in advance in solution A, or i) carbonic acid, ii) hydrogencarbonic acid, iii) carbonic acid and hydrogencarbonic acid solutions may be added during addition of mixed B1 and B2 solutions to solution A to maintain high molar concentration of carbonic acid and/or hydrogencarbonic acid ions in the reaction mixture.

The carbonic acid and/or hydrogencarbonic acid to be added in the present invention may be used in acid form or in water soluble salts form. Iron is generally added as a water soluble salt. In addition, i) carbonic acid and/or hydrogencarbonic acid, ii) iron, and iii) caseins to be used may be added in solutions or in solid state such as salts. Furthermore, solid i) carbonates and/or hydrogencarbonates, ii) iron, and iii) caseins may be simultaneously dissolved. However, a procedure to give solutions solely containing i) carbonates and/or hydrogencarbonates and ii) iron must be avoided.

Caseins applicable in the present invention may be illustrated with casein, acid casein, Sodium caseinate, lactic acid casein, α-casein, β-casein and κ-casein isolated from secretions such as milk of mammals including human being and cow. A number of methods have been known to massively isolate these caseins and any method can be used. Also, caseins prepared by gene technology using microorganisms, animal cells or transgenic animals can be used.

In addition, when crude caseins including mixtures of α-casein, β-casein and κ-casein are used, the molar concentration of caseins dissolved can be calculated from the average molecular weight obtained from their molar ratios.

Solution A containing carbonic acid or hydrogencarbonic acid includes carbonated water and solutions of ammonium hydrogencarbonate, sodium hydrogencarbonate, potassium hydrogencarbonate, sodium carbonate, calcium carbonate. A pH adjusting agent such as sodium hydroxide, ammonia, potassium hydroxide, hydrochloric acid, citric acid and lactic acid may be used singly or in combination. Components other than carbonic acid or hydrogencarbonic acid such as sugars, proteins and fats may also be contained in the solution A.

However, the molar concentration ratio of iron ion, and carbonic acid ion and hydrogencarbonic acid ion in the reaction mixture is important for the formation of carbonic acid- and/or hydrogencarbonic acid-iron-casein complexes without iron characteristic astringent taste. Hereinafter, test examples concerning to the above mentioned relationship are shown.

TEST EXAMPLE 1

Materials (Solution A) One liter each solution of sodium hydrogencarbonate of various molar concentrations.
(Solution B1) 0.2 L of ferric chloride solution.
(Solution B2) 0.8 L of one millimole of Sodium caseinate (Taiyo Chemical Co., Ltd.). However, the molar concentration was adjusted with the average molecular weight calculated from theoretical molecular weight based on the composition ratio of a α-casein, β-casein and κ-casein found by urea-sodium dodecylsulfate (SDS) electrophoresis.

Solution B was prepared by mixing solutions B1 and B2 and iron bound casein was prepared by adding one liter of solution B diluted with deionized water to solution A. Final molar concentration of hydrogencarbonic acid ion at 0.6 or over was adjusted by adding sodium hydrogencarbonate while mixing solutions A and B, or by adding in advance a required amount of sodium hydrogencarbonate in solution A to give saturated solution. These solutions were treated with 50,000 KD molecular weight cut off value to separate carbonic acid- and/or hydrogencarbonic acid-iron-casein complex from aqueous solution. No iron was detected by determination of the filtrate with an atomic absorption analysis (ICP) indicating that all iron component participated in formation of the complexes. Then, the complexes were diluted with a simulated liquid meal buffer containing 0.05 mole/L of imidazole, 0.15 mole/L of sodium chloride and adjusted at pH 7.5 (simulated buffer) to make 3.6 millimoles/L of iron concentration and heat sterilized at 90° C. for 10 minutes.

A below mentioned sensuous evaluation test was carried out for the resultant solutions. Panelists with 10 males and 10 females were given the test solutions to determine whether they sensed astringent taste or not using the simulated buffer solution as a control. A blindfold was given to each panelist so as not to disturb the result of sensuous evaluation test by appearance of test solutions. The sensuous evaluation test of one sample was carried out in the order of the control and the test solution. At least one day passed between sample testing. In addition, evaluation of each sample was performed in random order for each panelist to avoid between-day variation. The results of the sensuous evaluation test are shown in Table 1. The minimum molar concentration ratio of hydrogencarbonic acid ion/iron ion was calculated by dividing the molar concentration of hydrogencarbonic acid ion in a mixture of solutions A and B with the molar concentration of iron ion in solution B.

TABLE 1

B1 solution containing 16 millimoles of iron

| Molar concentration of hydrogencarbonic acid ion | | Number of panelist who sensed astringent taste | Minimum molar concentration ratio of $HCO_3$ ion/iron ion |
|---|---|---|---|
| Solution A | Solution A + B | | |
| 1.0 | 0.5 | 0 | 16.67 |
| 0.8 | 0.4 | 0 | 13.33 |
| 0.6 | 0.3 | 2 | 10.00 |
| 0.4 | 0.2 | 4 | 6.67 |
| 0.2 | 0.1 | 4 | 3.33 |
| 0.1 | 0.05 | 20 | 1.67 |

TABLE 2

B1 solution containing 200 millimoles of iron, Solution B: was diluted to 20-fold volume (10 millimole/L of iron is contained in solution B)

| Molar concentration of hydrogencarbonic acid ion | | Number of panelist who sensed astringent taste | Minimum molar concentration ratio of $HCO_3$ ion/iron ion |
|---|---|---|---|
| Solution A | Solution A + B | | |
| Saturated* | Saturated | 0 | 120 or over |
| Saturated | 1.2 | 0 | 120 |
| Saturated | 1.0 | 0 | 100 |
| Saturated | 0.8 | 1 | 80 |
| Saturated | 0.7 | 1 | 70 |
| 1.2 | 0.6 | 1 | 60 |
| 1.0 | 0.5 | 2 | 50 |
| 0.6 | 0.3 | 2 | 30 |
| 0.3 | 0.15 | 3 | 15 |

*Saturated at 30° C.

As shown above, increased iron concentration in solution B1, also requires increased hydrogencarbonic acid ion. As described above, preparation of carbonic acid- and/or hydrogencarbonic acid-iron-casein complexes by addition of solution B in solution A requires at least three molecules, preferably 10 or more molecules of carbonic acid and/or hydrogencarbonic acid molecules to the added one atom of iron. Furthermore, binding of more than 200 atoms of iron to one molecule of caseins demands the presence of 30 molecules or over, preferably 60 molecules or over, more preferably 100 molecules or over of carbonic acid and/or hydrogencarbonic acid to one molecule of caseins.

The iron compound applicable for use in the present invention may be illustrated with, for example, trivalent iron compounds such as ferric chloride, ferric nitrate and ferric sulfate, and bivalent iron compounds such as ferrous nitrate, ferrous sulfate and ferrous citrate. The amount of iron to be added based on one mole of caseins is preferably 10 moles or over, more preferably 16 moles or over, far more preferably 46 moles or over, up to 1,000 moles or less, preferably 500 moles or less, and more preferably 250 moles or less. Hereinafter, a test example which shows above mentioned relationship will be illustrated.

TEST EXAMPLE 2

Materials (Solution A) One liter solution containing 1,200 millimoles/L of sodium hydrogencarbonate.
(Solution B1) 0.2 L solutions each containing respective molar concentration of ferric chloride.

(Solution B2) 0.8 L solution containing one millimole of lactic acid casein (New Zealand, Dairy Board Co., Inc.). However, the molar concentration of lactic acid casein is calculated in a similar manner with that of Test example 1. Lactic acid casein is dissolved in a very small amount of 1N sodium hydroxide solution and diluted with deionized water.

Solutions B1 and B2 were mixed to give solution B, and one liter of solution B was added to solution A to give iron bound caseins. In addition, solution B is diluted with deionized water at need to make final molar concentration ratio of iron ion/caseins at 100 or over. These solutions were hydrated and desalted with a molecular weight 5,000 cut ultrafiltration membrane and concentrated. The concentrated solution was diluted to make iron concentration of 3.6 millimoles/L with the simulated buffer and sterilized at 90° C. for 10 minutes. The resultant solutions were subjected to a sensuous evaluation test in a similar manner with that of Test example 1. The results are shown in Table 3.

TABLE 3

| Molar ratio of iron ion/caseins | Number of panelists who experienced astringent taste |
|---|---|
| 1 | 5 |
| 10 | 4 |
| 16 | 3 |
| 46 | 2 |
| 81 | 1 |
| 100 | 0 |
| 250 | 1 |
| 500 | 2 |
| 1000 | 4 |
| 1200 | 20 |

As shown above, the astringent taste of iron may be diminished in some amount of iron bound with caseins. Above results show that the amount of iron the preparation of carbonic acid- and/or hydrogencarbonic acid-iron-casein complex should be preferably 10 moles or over, more preferably 16 moles or over, far more preferably 46 moles or over as iron ion to one mole of caseins, and the upper limit should be 1,000 moles or less, preferably 500 moles or less, more preferably 250 moles or less.

BEST MODES FOR CARRYING OUT THE PRESENT INVENTION

EXAMPLE 1

One liter solution containing 1.2 moles of sodium hydrogencarbonate and 10 micromoles of $\alpha$-casein (Sigma Chemical Co.) (Solution A), and one liter solution containing 1.5 millimoles of ferric sulfate as an iron ion (Solution B) were prepared. Then, solution B was added to solution A to give iron bound $\alpha$-casein. The resultant solution was desalted and concentrated with a molecular weight 5,000 cut ultrafiltration membrane, and diluted with the simulated buffer to make iron content of 26 mg/100 ml. The diluted solution was filled and sealed in a test tube equipped with a screw cap, and heated at 90° C. for 10 minutes. After heating, the solution was allowed to cool to room temperature and kept for a month at room temperature. The solution was subjected to the sensuous evaluation test in a similar manner with that of Test example 1 with 20 panelists and no panelist experienced astringent taste.

EXAMPLE 2

One liter solution containing 0.5 mole/L each of sodium carbonate and sodium hydrogencarbonate, adjusted at pH 8.2 with acetic acid (Solution A), one liter solution containing 1.5 millimoles of ferric nitrate as an iron ion (Solution B1), and 10 micromoles of powder form $\alpha$-casein (Sigma Chemical Co.) (B2) were prepared. Then, solution B1 and B2 were added to solution A to give iron bound $\alpha$-casein. The resultant solution was desalted and concentrated with a molecular weight 5,000 cut ultrafiltration membrane, and diluted with the simulated buffer to make iron content of 26 mg/100 ml. The diluted solution was filled and sealed in a test tube equipped with a screw cap, and heated at 90° C. for 10 minutes. After heating, the solution was allowed to cool to room temperature and kept for a month at room temperature. The solution was subjected to the sensuous evaluation test in a similar manner with that of Test example 1 with 20 panelists and no panelist experienced astringent taste.

EXAMPLE 3

One liter solution containing 1.5 moles/L of sodium carbonate adjusted at pH 8.0 with hydrochloric acid (Solution A), 0.2 L solution containing 1.5 millimoles of iron citrate as an iron ion (Solution B1), and 0.8 L solution containing 10 micromoles of $\kappa$-casein (Sigma Chemical Co.) (Solution B2) were prepared. Then, solutions B1 and B2 were mixed and solution A was added to the mixed solution to give iron bound $\kappa$-casein. The resultant solution was desalted and concentrated with a molecular weight 5,000 cut ultrafiltration membrane, and diluted with the simulated buffer to make iron content of 26 mg/100 ml. The diluted solution was filled and sealed in a test tube equipped with a screw cap, and heated at 90° C. for 10 minutes. After heating, the solution was allowed to cool to room temperature and kept for a month at room temperature. The solution was subjected to the sensuous evaluation test in a similar manner with that of Test example 1 with 20 panelists and no panelist experienced astringent taste.

TEST EXAMPLE B3

The solution prepared in Example 1 (Test group) and a ferrous sulfate solution (Control group 1) were dissolved in a phosphate buffer saline (pH 7.2) containing 6.2 mg/100 g of ascorbic acid and sodium ascorbate as vitamin C to make iron concentration of 20 mg/100 ml, and the resultant solution was heated at 90° C. for 10 minutes to give a test sample. In addition, a phosphate buffer saline (pH 7.2) containing 6.2 mg/100 g of vitamin C was heated at 90° C. for 10 minutes to give an another test sample as Control group 2.

Female Wistar rats, 21-day-old immediately after weaning (Charles River Japan, Inc.) and body weight of 45–50 g were selected and fed with iron deficient feed (Oriental Yeast Co., Ltd., iron content of 0.25 mg/100 g feed) for two weeks to give anemia rats with blood hemoglobin content of 7 g/100 ml or less. One group was made with 5–8 rats, and test sample was given by gavage at a rate of 1 ml/day for 6 weeks under feeding with the iron deficient feed. On week 6 after the start of administration of test sample, blood was drawn from tail vein and hemoglobin content was determined with an automatic cell counter (Toa Medical Electronics Co., Ltd.). The results are shown in Table 4.

TABLE 4

| | Hemoglobin content (Average ± SD) (g/100 ml) |
|---|---|
| Test group | 17.2 ± 1.3 |
| Control group 1 | 13.0 ± 0.9 |
| Control group 2 | 4.9 ± 0.4 |

As shown above, the carbonic acid- and/or hydrogencarbonic acid-iron-casein complexes of the present invention exhibit effect for treatment of anemia, and the effect is superior than that of inorganic iron, ferrous sulfate.

INDUSTRIAL APPLICABILITY

The carbonic acid- and/or hydrogencarbonic acid-iron-casein complexes of the present invention show no iron characteristic astringent taste even after heat sterilization, and are useful for prevention and treatment of anemia and as raw materials of foods, medicines and feeds.

We claim:

1. A heat-resistant carbonic acid- or hydrogencarbonic acid-iron-casein complex comprising:

at least one molecule of casein;

at least one molecule of carbonic acid, hydrogencarbonic acid, or a combination thereof per molecule of casein; and approximately 1–1,000 atoms of iron;

wherein said carbonic acid- or hydrogencarbonic acid-iron-casein complex is heat resistant.

2. The heat resistant carbonic acid- or hydrogencarbonic acid-iron-casein complex of claim 1, wherein the casein/iron/carbonic acid or hydrogencarbonic acid ratio is approximately 1/200/30–100.

3. The heat resistant carbonic acid- or hydrogencarbonic acid-iron-casein complex of claim 1, wherein said casein is selected from the group consisting of casein, acid casein, sodium caseinate, lactic acid casein, $\alpha$-casein, $\beta$-casein, and $\kappa$-casein.

4. The heat resistant carbonic acid- or hydrogencarbonic acid-iron-casein complex of claim 1, wherein the amount of iron per mole of casein is between approximately 46 moles and 250 moles.

5. The heat-resistant carbonic acid- or hydrogencarbonic acid-iron-casein complex of claim 1, wherein said complex is heat sterilized.

6. The heat-resistant carbonic acid- or hydrogencarbonic acid-iron-casein complex of claim 4, wherein said sterilization results from heating said complex to approximately 90° C. for about 10 minutes or approximately 120° C. for about 2–3 seconds.

7. The heat-resistant carbonic acid- or hydrogencarbonic acid-iron-casein complex of claim 1, wherein said complex lacks iron astringent taste.

8. A method of producing carbonic acid- or hydrogencarbonic acid-iron-casein complex, said complex comprising at least one molecule of casein; at least one molecule of carbonic acid, hydrogencarbonic acid, or a combination thereof per molecule of casein; and approximately 1–1,000 atoms of iron, said method comprising the steps of:

a) preparing a solution containing an acid selected from the group consisting of carbonic acid or hydrogencarbonic acid, or a combination thereof;

b) preparing a solution containing iron and casein, thereby forming a iron-casein solution; and c) mixing said iron-casein solution with said solution containing acid, thereby forming an aqueous solution of said complex;

wherein the molar concentration of iron ion in said iron solution is between approximately 1% and 33% of the molar concentration of acid in said aqueous solution of carbonic acid- or hydrogencarbonic acid-iron-casein complex.

9. A method of producing a heat resistant carbonic acid- or hydrogencarbonic acid-iron-casein complex, said complex comprising at least one molecule of casein; at least one molecule of carbonic acid, hydrogencarbonic acid, or a combination thereof per molecule of casein; and approximately 1–1,000 atoms of iron said method comprising the steps of:

a) preparing a solution containing an acid selected from the group consisting of carbonic acid or hydrogencarbonic acid, or a combination thereof, and casein, thereby forming an acid-casein solution;

b) preparing a solution containing iron; and c) mixing said acid-casein solution with said solution containing iron, thereby forming an aqueous solution of said complex;

wherein the molar concentration of iron ion in said iron solution is between approximately 1% and 33% of the molar concentration of acid in said aqueous solution of carbonic acid- or hydrogencarbonic acid-iron-casein complex.

10. The method of producing a heat resistant carbonic acid- or hydrogencarbonic acid-iron-casein complex of claim 8 or 9, wherein the casein/iron/carbonic or hydrogencarbonic acid ratio is approximately 1/200/30–100.

11. The method of producing a heat resistant carbonic acid- or hydrogencarbonic acid-iron-casein complex of claim 8 or 9, wherein the molar concentration of iron ion in said iron solution is approximately 1% of the molar concentration of acid in said aqueous solution of carbonic acid- or hydrogencarbonic acid-iron-casein complex.

12. The method of producing a heat resistant carbonic acid- or hydrogencarbonic acid-iron-casein complex of claim 8 or 9, further comprising the step of:

filtering said aqueous solution of said complex through a membrane with a molecular weight cutoff value of approximately 5,000 kD, thereby forming a filtrate.

13. The method of producing heat resistant carbonic acid- or hydrogencarbonic acid-iron-casein complex of claim 8 or 9, wherein the iron used in preparing said solution containing iron is a trivalent iron compound selected from the group consisting of ferric chloride, ferric nitrate, and ferric sulfate.

14. The method of producing heat resistant carbonic acid- or hydrogencarbonic acid-iron-casein complex of claim 8 or 9, wherein the iron used in preparing said solution containing iron is ferric chloride.

15. The method of producing heat resistant carbonic acid- or hydrogencarbonic acid-iron-casein complex of claim 8 or 9, wherein the iron used in preparing said solution containing iron is a bivalent iron compound selected from the group consisting of ferrous nitrate, and ferrous sulfate, and ferrous citrate.

16. The method of producing heat resistant carbonic acid- or hydrogencarbonic acid-iron-casein complex of claim 8 or 9, wherein the iron used in preparing said solution containing iron is ferrous citrate.

17. The method of producing heat resistant carbonic acid- or hydrogencarbonic acid-iron-casein complex of claim 8 or 9, wherein the acid used in preparing the said solution containing acid is selected from the group consisting of carbonated water and ammonium hydrogencarbonate, sodium hydrogencarbonate, potassium hydrogen carbonate, sodium carbonate, calcium carbonate and mixtures thereof.

18. A method of treating anemia in a mammal, comprising administering a therapeutically effective amount of the complex of claim 1 to an anemic mammal.

19. A method of increasing hemoglobin content in the blood of a mammal, comprising administering the complex of claim 1 to said mammal in an amount effective to increase hemoglobin content.

* * * * *